United States Patent [19]

Sohval et al.

[11] Patent Number: 4,592,079
[45] Date of Patent: May 27, 1986

[54] MEDICAL IMAGING DEVICE USING TRIGGERED PLASMA CATHODE FLASH X-RAY SOURCES

[75] Inventors: A. Robert Sohval, Cambridge, Mass.; Gerald Cooperstein, Rockville; Shyke A. Goldstein, Gaithersburg, both of Md.; David R. Hearn, Wellesley, Mass.

[73] Assignee: Elscint Ltd., Haifa, Israel

[21] Appl. No.: 313,268

[22] Filed: Oct. 21, 1981

[51] Int. Cl.⁴ ............................ A61B 6/02; H05G 1/70
[52] U.S. Cl. ................................... 378/9; 378/10; 378/106; 378/122; 313/547; 315/330
[58] Field of Search ................. 378/9, 10, 106, 122; 315/330; 313/547

[56] References Cited

U.S. PATENT DOCUMENTS

| | | | |
|---|---|---|---|
| 3,465,192 | 9/1969 | Lafferty | 313/547 |
| 3,970,884 | 7/1976 | Golden | 313/55 |
| 4,129,783 | 12/1978 | Houston | 250/445 |
| 4,223,225 | 9/1980 | Laffitte et al. | 250/445 |
| 4,289,969 | 9/1981 | Cooperstein et al. | 378/9 |

FOREIGN PATENT DOCUMENTS 2025729  1/1980  United Kingdom ................ 378/10

OTHER PUBLICATIONS

"Three-Dimensional Imaging of Heart, Lungs, and Circulation"—Science—vol. 210, Oct. 17, 1980-pp. 273-280.
Capacitor Discharge Engineering—by Frank B. A. Frungel, Academic Press, N.Y., 1976.

Primary Examiner—Alfred E. Smith
Assistant Examiner—T. N. Grigsby
Attorney, Agent, or Firm—Sandler & Greenblum

[57] ABSTRACT

A medical imaging device employs a plurality of triggered plasma cathode flash X-ray sources, each of which has an axially extending round anode rod, a cathode, and a trigger electrode. The application of a trigger pulse between the electrode and the cathode produces a burst of plasma near the cathode, the plasma containing electrons that are accelerated toward and impact the anode in a region termed the "focal spot" for producing X-rays when a voltage source applies a predetermined voltage between the cathode and anode. According to the invention, a non-conducting surface interconnects the electrode with a cathode or a conductor held at the same potential as the cathode, the application of a trigger pulse to the electrode causing flashover across said surface for producing the burst of plasma.

24 Claims, 18 Drawing Figures

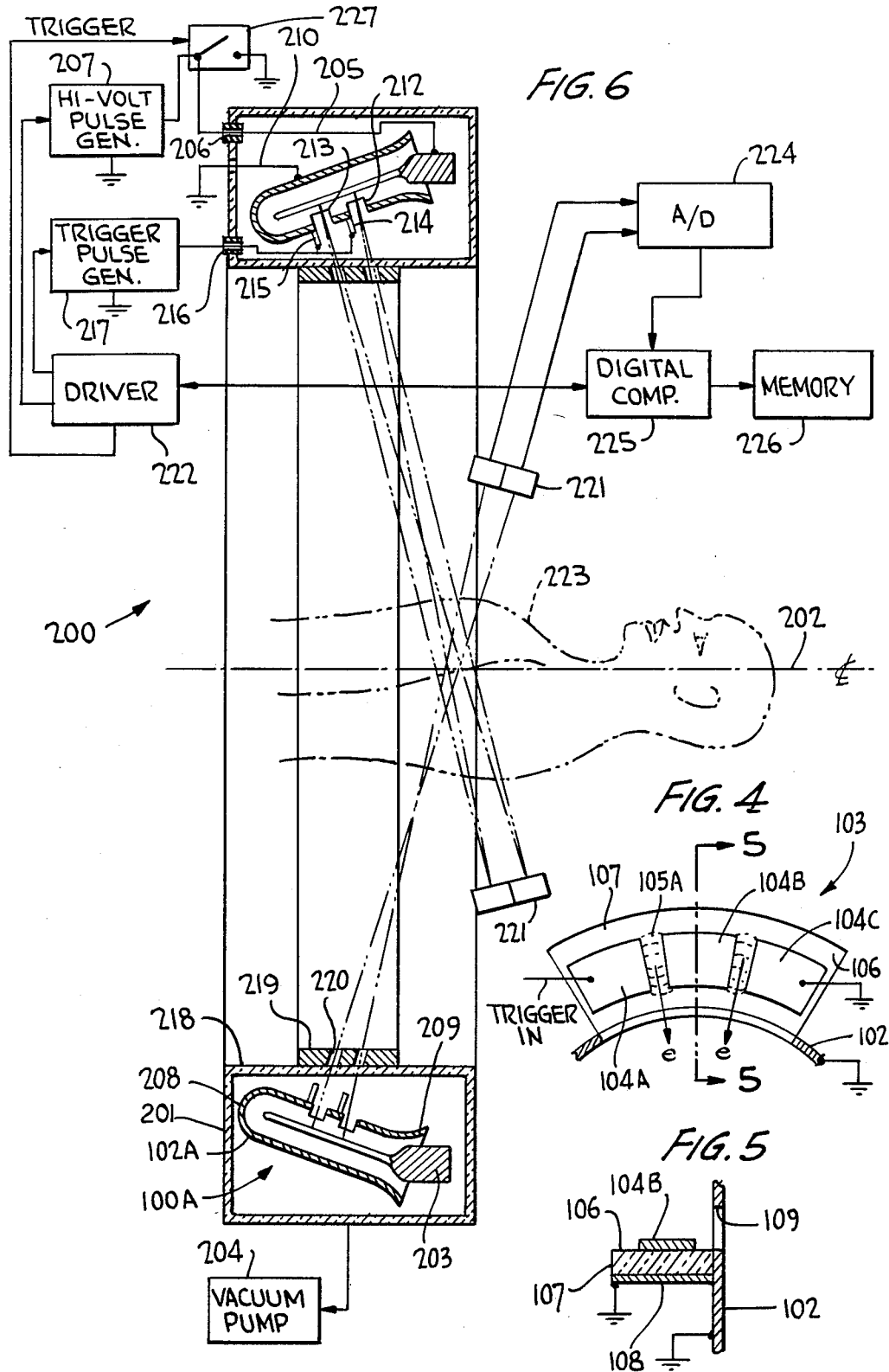

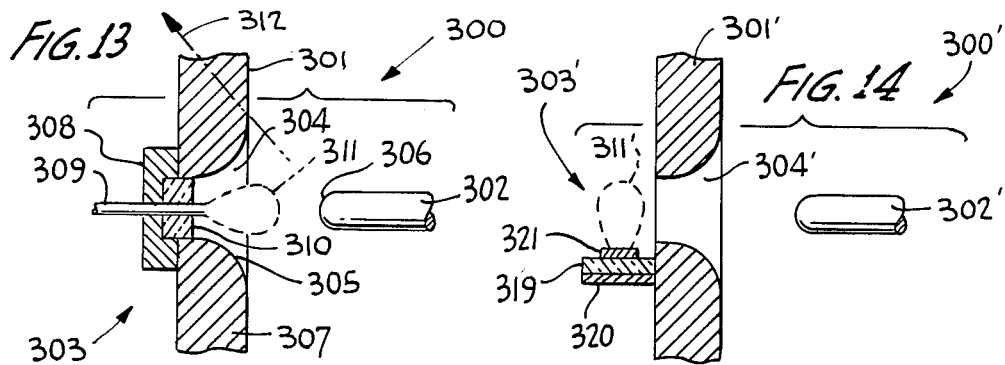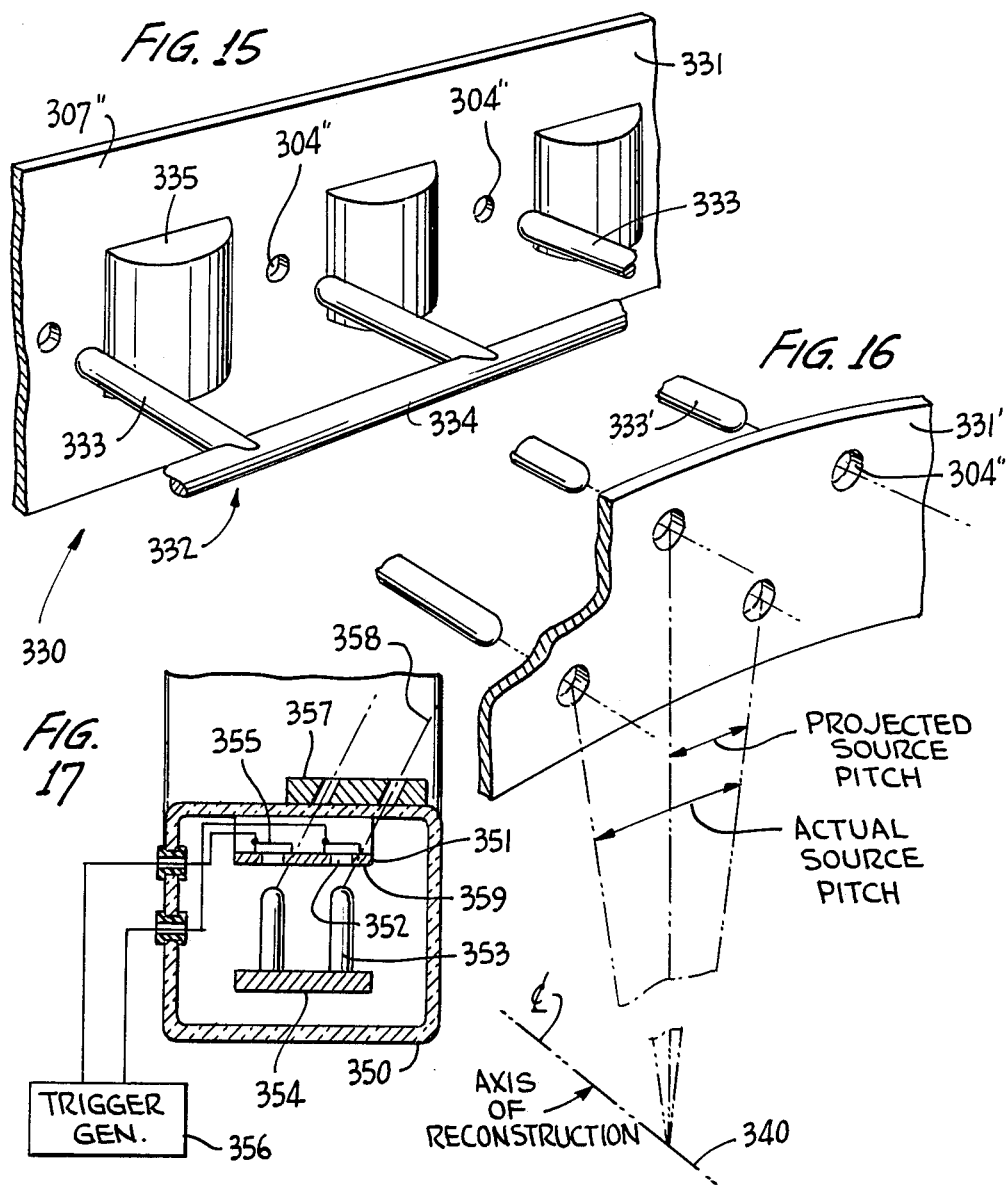

MEDICAL IMAGING DEVICE USING TRIGGERED PLASMA CATHODE FLASH X-RAY SOURCES

DESCRIPTION

TECHNICAL FIELD

This invention relates to a medical imaging device, such as a CT scanner, using triggered flash X-ray sources for obtaining data by which a planar slice through a body under examination can be reconstructed in terms of its X-ray absorption characteristics.

BACKGROUND ART

X-ray imaging devices operating on the principle of computerized tomography (CT) usually utilize a single X-ray source that moves about a body under examination. The regimen followed can be a combination of linear translational and rotational movement of the source relative to the body, using a pencil or fan beam of X-rays, or pure rotational movement wherein a fan beam of radiation is used. The object of these scan regimens is to cause beams of X-rays in the plane of a slice through the body to pass through each elemental volume of the slice in many different directions, and to measure the intensity of the beams after they pass through the body. As is well known, various reconstruction algorithms are available to operate on data so obtained in order to calculate the absorption distribution of radiation in each elemental volume of the slice, and to provide from the computations a two-dimensional display of the slice in terms of its X-ray absorption characteristic.

By reason of the mechanical movements required to effect a scan, the time required to complete a scan is large as compared to physiological movements of individual structural components of the circulatory and respiratory systems. As a consequence, conventional scanning techniques for imaging a beating heart, for example, result in blurred images because the heart moves through several cycles before the scan is complete. One approach to improve image quality is to synchronize the scan with a physiological parameter obtained from the patient, as, for example, in the case of a heart scan, a particular point in the cycle obtained from an EKG reading. In this way, data are recorded only at the same instant during each cycle of movement. While this improves image quality, the image so obtained is made up of data obtained over many heart cycles, and is not a true instantaneous image.

Another and more promising approach is to utilize a plurality of stationary X-ray sources substantially circularly arranged about a patient. By strobing the X-ray sources sequentially, a rotating fan beam of X-rays is generated. The speed at which the strobing occurs is much faster than the physiological movements under investigation, so that the resulting image is of improved quality because, it is obtained while the organ under consideration is substantially motionless. Such an approach is shown in U.S. Pat. No. 4,129,783 U.S. Pat. No. 4,223,225. In both of these patents, and in the so-called DSR system constructed at the Mayo Medical School and described in *Science*, Vol. 210, 17 October 1980 (pages 273–280), the X-ray sources are conventional hot-cat node X-ray tubes. The description in the '225 patent cited above indicates the use of tubes of 5 cm in diameter, but the source of tubes of this size is not identified. Furthermore, the description indicates that these tubes are placed at about 10° intervals in a circle about 1 m. in diameter. This arrangement provides for 36 tubes with sufficient space between adjacent tubes to permit detectors to be located therebetween. Because so few tubes are used, the image quality obtained is likely to be marginal. The DSR device, on the other hand, contemplates 28 rotating-anode, heavy-duty X-ray tubes distributed around 162° of arc, and rotatable at 15 RPM to permit more than 28 angles of view to be obtained. The diameter of the circle of reconstruction in this device is about 21 cm. Rotation of the gantry on which the X-ray tubes is mounted allows 112 angular views to be obtained in 1/15 second, thereby reducing artifacts from limited sampling and improving spatial resolution. This mode achieves a wider reconstruction field for objects up to 38 cm. in diameter.

Ideally, a CT scanner which requires no gantry rotation or indexing should have about 500 X-ray sources arranged in a circle in order to achieve high-quality images of the whole body; but 250 sources would probably be sufficient to effect high-quality images over a smaller region, such as the heart. The prior art, as evidenced by the above-described patents and the DSR device, do not approach either of these densities of sources. As a consequence, thought has been given to constructing a CT scanner with cold-cathode X-ray tubes, inasmuch as these tubes should be smaller in size and less expensive to produce than hot-cathode X-ray tubes. Cold-cathode diode tubes, such as shown in U.S. Pat. No. 3,970,884 which use a pointed anode rod and a cathode in form of graphite rings that encircle the point, are relatively small in size, but are not practical in view of the problems with isolating one source from the next when the sources are closely packed, and the difficulties and expenses of switching the high voltages required to obtain repeatability in the X-ray output from burst to burst.

Cold-cathode triodes such as are disclosed in U.S. Pat. No. 3,518,433 and in pages 241–253 of *CAPACITOR DISCHARGE ENGINEERING-VOL. III* by Frank B. A. Früngel (Academic Press, N.Y., 1976) appear to be more easily controllable, although their size appears to be comparable to conventional hot cathode X-ray tubes. Each of the triode types of X-ray sources utilizes an anode rod and a disk-like cathode. Considering the commercially available Früngel triode, it probably could be repackaged in a scanner such that each source would require from 6–8 cm diameter in order to yield about sources 80 sources in a circle about 1.5 m. in diameter.

This number of sources would still require rotating or indexing the gantry to provide an adequate number of views, but the spectral and spatial stability of such tubes when used in a CT environment remains unknown. Furthermore, the problem of shielding anodes of sources adjacent to the anode of the source that is pulsed to produce X-rays remains to be solved. The latter is a formidable problem unless only that anode/-cathode pair whose trigger is strobed has a high voltage applied therebetween. If all of the anodes were maintained at a high voltage, stray electrons from a burst of plasma produced by the pulsed source may impact another anode together with secondary electrons produced by U-V radiation thereby causing unwanted X-ray emissions from anodes other than the desired one.

Another disadvantage of the Früngel type of triode is the relatively large trigger voltage required, typically several tens of kV. This increases the cost and complexity of a CT scanner system employing this type of X-ray source.

Thus, despite a well-known need for a CT scanner with a number of X-ray sources sufficient to eliminate the need for indexing, no successful source or scanner is currently available. It is, therefore, an object of the present invention to provide a new and improved tomographic scanner using cold-cathode flash X-ray sources wherein the above-described deficiencies are overcome or substantially reduced.

DISCLOSURE OF INVENTION

A CT scanner, according to the present invention, icludes a plurality of triggered plasma cathode X-ray sources arrayed about an axis of the scanner, and an electrical network for selectively triggering the sources. Each source has an anode and a cathode; and the electrical network has means for establishing a predetermined voltage between all of the anodes as a group and all of the cathodes as a group. A separate trigger system is associated with each source, each trigger system being constructed and arranged so that surface flashover occurs in response to the application of a trigger pulse to the trigger system of a selected source for creating a burst of plasma containing electrons adjacent the cathode of the selected source. The predetermined voltage between anode and cathode of the selected source causes electrons in the plasma to be accelerated toward and impact on the anode of the selected source thereby producing X-rays.

Surface flashover, which describes a relatively low voltage breakdown, usually several kV, across a gap defined by an insulating surface, provides a well-defined origin for the plasma; and the orientation of the surface establishes the direction in which the plasma is launched.

In general, the plasma generated by surface flashover expands, primarily in a direction normal to the non-conducting surface, with a velocity of approximately 2 cm/$\mu$sec. If it expands towards the anode, the diode impedance, which is initially high, will collapse to a short circuit in about 0.5 $\mu$sec if the anode-cathode gap is 1 cm. When the power supply that impresses high voltage across the anode-cathode space is a high-voltage pulse-forming network (PFN), two modes of operation are possible:

Mode I $t_s \leq t_1$

Mode II $t_s \gg t_1$ where $t_s$ is the characteristic pulse length of the high-voltage pulse from the power supply, and $t_1$ is the characteristic time for impedance collapse of the diode load.

In Mode I, the trigger is usually fired before the high voltage reaches its peak value. Once triggered, the diode impedance begins to fall, but maintains a finite value (usually a few hundred to a few thousand ohms), and does not collapse until after the high-voltage pulse has terminated. In this mode, the output X-ray flux is strongly dependent on diode impedance. If the impedance is too high, the current is low and the flux is low. If the impedance is too low, the load voltage is low and the flux is low. The output flux is maximized if the average load impedance is about 3 times the source impedance.

In Mode II, an energy storage device such as a capacitor is generally charged to high voltage before the trigger is fired. The diode impedance is initially high, as previously indicated, but eventually collapses as the plasma bridges the anode-cathode gap, discharging the capacitor. In this case, the output flux and its spectral content can be shown to be essentially independent of the time history of the diode impedance and functions only of the capacitance and initial charging voltage. Thus, the diode output is intrinsically stable in this case.

Some of the relative advantages of Mode I operation are (a) the diode impedance is controlled and relatively constant (with respect to Mode II), allowing for maximum energy transfer to the load or maximum output flux per unit energy transfer; and (b) anode damage is reduced because anode damage is preferentially caused by bombardment of low voltage electrons, and in Mode I operation, only minimal electron flow occurs at low voltage because the high-voltage pulse terminates before the diode impedance collapses.

Some of the relative advantages of Mode II operation are (a) a high-voltage PFN with long rise and fall times is easier and less expensive to construct; and, (b) the X-ray output of the diode is relatively stable and insensitive to diode impedance behavior.

In order to reduce anode damage when operating in Mode II, a crowbar switch may be used to divert the energy stored in the PFN away from the anode when the diode impedance collapse has reduced the PFN voltage below a specified value of the order of 100 KV.

The point of origin of the surface flashover and its launch direction influence both the spectral and spatial characteristics of an X-ray burst produced as a consequence of the generation of the plasma, and the reproducibility of the characteristics of the X-rays from burst to burst. This is especially true in Mode I operation described above, and also applies to a lesser degree to Mode II operation. Thus, the invention also contemplates controlling the direction in which the plasma burst is launched. Where the non-conductive surface has a portion whose normal is directed toward the anode, at least some of the plasma will be launched toward the anode. Experimentally, it has been found that if a substantial portion of the plasma is directed toward the anode, very large spikes in the cathode-to-anode current may be produced which can adversely affect both the spectral stability and the reproducibility of the resultant X-rays. A reduction in stability and reproducibility reduces the quality of image reconstruction when sources so constructed are used in CT applications, although these parameters do not affect the ability of the X-ray source to satisfactorily perform as part of a shadowgraphic device.

In another arrangement, the non-conducting surface has a portion whose normal is inclined away from the anode. When plasma is not launched directly toward the anode, the initial flux (i.e., the current output, and hence the amount of X-rays) is reduced. In this case, the initial flux can be increased by increasing the number of plasma sources; i.e., by constituting the electrode as a plurality of conductive pads separated by portions of the non-conducting surface. Increasing the number of gaps increases the quanitity and effective area of the plasma source of electrons, which in turn increases the quantity of electrons which can flow to the anode and produce X-rays. In such case, the trigger pulse is applied to at least one of the pads, and at least one of the other pads constitutes the conductor which is held at the same potential as the cathode. Flashover occurs at the gaps between the pads when a trigger pulse is applied. With this arrangement, the gaps can be distributed angularly about the axis of the anode for increasing the flux produced by the anode.

The present invention also provides for de-enhancement of the electric field lines at the cathode in order to suppress spurious breakdown due to field concentration and in order to suppress the production of spurious X-rays from sources adjacent the source that is triggered. In one embodiment, the cathode is a cylindrical metallic sleeve transparent to X-rays, the axis of the sleeve coinciding with the axis of the anode which is shaped like a rod. Furthermore, the sleeve is apertured in the vicinity of the plasma source which is located outside the sleeve. This arrangement has the advantage of controlling the direction of launching of the plasma.

In addition to providing de-enhancement of the electric field lines at the cathode and enhancement of the focusing of electrons in the space between the cathode and the anode, the cathode sleeve serves to shield the anode of an adjacent source from UV radiation and electrons produced by the plasma of a given source. The latter feature is important when the X-ray sources according to the present invention are packed in a circle around an axis and are to be used as part of a CT scanner.

In another form of the invention, the source is provided with a second triggered plasma source axially displaced from the first-mentioned triggered plasma source, and a second non-conducting surface interconnects a second trigger electrode with the cathode or a second conductor held at the same potential as the cathode. With this arrangement, the focal spot on the anode arising from the application of a trigger pulse of the second electrode is axially displaced from the focal spot arising from the application of the trigger pulse to the first-mentioned electrode. In general, the invention provides for a plurality of trigger electrodes producing a plurality of focal spots on an anode. When a source of this nature is utilized in a CT scanner, multiple slices through a patient can be obtained simultaneously, or in rapid succession, without indexing the patient.

When the cathodes of the sources are cylindrical sleeves, one end of each cathode may be closed by a hemispherical dome, and the other end may be provided with an outwardly flaring skirt. This configuration of the cathode permits the anode to be supported in cantilever fashion adjacent the flaring skirt, and provides the desirable electron focusing and de-enhancement of the electric field lines.

Sources constructed in this manner can be packed around the axis of the scanner with the hemispherical domes of the sleeves facing in the same direction. However, the skirts of the sleeves will also face in axial direction, and the presence of the skirts will require the spacing between the anodes of adjacent sources to exceed the diameter of the sleeves. In order to increase the density of packing, the direction of adjacent cathode sleeves can be reversed. That is to say, the domes of adjacent sources face in opposite directions. Finally, the rows of anodes can be staggered to increase the packing density.

In another embodiment, the cathode is a metallic plane normal to the axis of a rod-like anode. This arrangement has the advantage of further reducing the electric field at the cathode, hence reducing spurious firings, and also permitting dense spacing of the anodes in a multi-anode linear array in a CT scanner. The cathode plate, which is thin and transparent to X-rays, is apertured in the vicinity where the anode rod, if extended, would intersect the cathode plate. Located in the aperture, below the surface of the cathode, is a non-conducting surface and a trigger electrode. This arrangement also has the advantage of controlling the direction of launching of the plasma.

In another form of this invention, multiple-anode arrays can be configured in a staggered array in which the projected source pitch, as seen from the center of the reconstruction circle, is maintained at its nominal value while the actual distance between anodes is increased by at least 50%. This arrangement has the advantage of reducing spurious X-ray flux caused by electrons flowing to nearby anodes.

In another embodiment, multiple linear anode arrays may be axially displaced in the CT scanner. Each anode has its own surface-flashover trigger. Utilization of this type of radiation source in a CT scanner allows multiple slices through a patient to be obtained in simultaneously or in rapid succession, without mechanically indexing the patient.

BRIEF DESCRIPTION OF DRAWINGS

Embodiments of the present invention are shown in the accompanying drawings, wherein:

FIG. 4 is a plan view of one of the triggers shown in FIG. 3;

FIG. 5 is a sectional view taken along the line 5—5 of FIG. 4; FIG. 6 is a schematic cross-sectional view of a scanner according to the present invention utilizing the embodiment of a triggered plasma cathode flash X-ray source shown in FIG. 3;

FIG. 13 is a cross-section of another embodiment of an X-ray source according to the present invention;

FIG. 14 is a cross-section of a still further embodiment;

FIG. 15 is a perspective of a development of a plurality of sources like those shown in FIGS. 13 and 14 as employed in a CT scanner;

FIG. 16 is a further perspective like FIG. 15 but showing a more densely packed arrangement of sources; and FIG. 17 is a cross-sectional view of an annular envelope containing the source configuration shown in FIG. 15.

DESCRIPTION OF PREFERRED EMBODIMENTS

Figure 1:
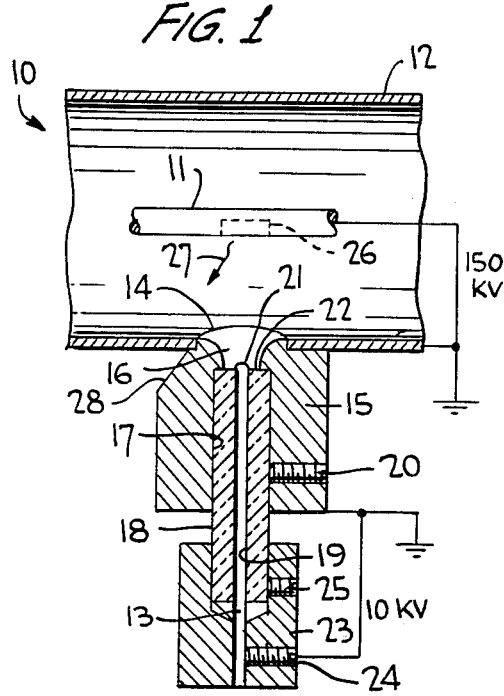
FIG. 1 is a sectional view of an X-ray source according to the present invention showing surface flashover triggering.

Referring now to FIG. 1 of the drawings, reference numeral 10 designates one embodiment of a triggered plasma cathode flash X-ray source according to the present invention. Source 10 comprises an axially extending round anode rod 11, cathode 12 in the form of a cylindrical sleeve coaxial with the rod, and trigger electrode 13, all of which are encased in an evacuated envelope (not shown). Rod 11 is of high-Z material such as tungsten, and has a diameter from 1-4 mm. The length of the anode rod is from 1-20 cm; and the rod is supported in cantilever fashion from an anode bus (not shown).

Sleeve 12 is composed of a low-Z material, such as aluminum, which is transparent to X-rays, and has a diameter from 2-3 cm. The cathode sleeve has a hemispherical dome at one end (not shown in FIG. 1) and an outwardly flaring skirt (not shown in FIG. 1) at the opposite end where the anode rod is connected to the anode bus.

Cathode sleeve 12 is apertured at 14 to receive metallic support 15 mechanically and electrically connected to sleeve 12 in the region of aperture 14. Support 15 extends substantially radially with respect to the axis of rod 11 and has opening 16 having a large radius of curvature as shown in FIG. 1 which connects the interior of sleeve 12 with axially extending bore 17 in the support. Insulator 18, having a centrally located axially extending bore 19, is mounted in counter-bore 17 and held there by set screw 20. Trigger 13, which is cylindrical, is press-fitted into bore 19 in insulator 18 such that hemispherically shaped free end 21 of the trigger electrode is located about 1-1.5 cm from the anode, but is entirely outside the cathode sleeve as shown in FIG. 1.

Axial end 22 of insulator 18 defines a non-conducting surface that interconnects free end 21 of electrode 18 to support 15, which constitutes a conductor held at the same potential as the cathode by reason of the mechanical interconnection between the support and the cathode.

The end of trigger 13 opposite end 21 extends beyond insulator 18 and terminates in metal cap 23, which is held thereto by set screw 24, cap 23 being held to insulator 18 by set screw 25.

In operation, a high-voltage pulse, about 150 KV, is applied between anode 11 and cathode 12, which may be at ground potential as shown in FIG. 1. During the existence of the high-voltage pulse between the anode and the cathode, a relatively small trigger pulse, say from 2-15 KV, is applied to trigger 13 by way of set screw 24. The polarity of the trigger depends upon the configuration of the diode. As a consequence of the trigger pulse, surface flashover occurs between end 21 of trigger 13 and support 15 across surface 22 of insulator 18, producing a burst of plasma that expands from surface 22 in the direction of the normal to surface 22 with a characteristic speed of about 2 cm./$\mu$sec, the speed being dependent on the trigger voltage.

The burst of plasma contains electrons that are accelerated toward and impact the anode in a semicylindrical region thereof designated by reference numeral 26 and termed the "focal spot". The focal spot, which extends along the surface of anode 11 facing the source of electrons, will have a width substantially equal to the diameter of the anode rod, and a length comparable to the anode to cathode distance. By reason of the high voltage between the anode and the cathode, electrons impacting the anode on the focal spot have sufficient energy to produce X-rays, which radiate from the spot in all directions. Being transparent to X-rays, cathode 12 passes these X-rays. For reasons indicated below, a fan beam of X-rays 27 are in the preferred direction; and, for this reason, a portion 28 of support 15 is removed in order to provide a direct path for these X-rays. X-rays in other directions are shielded by a lead barrier (not shown).

By locating anode 11 centrally in cathode 12, the electric field lines within the cathode sleeve due to the high voltage between the anode and cathode are radially oriented in a plane perpendicular to the axis of the anode. To prevent enhancement of the field lines in the vicinity of aperture 16 in the cathode, a large radius is provided in support 15 defining the aperture. As a consequence, a large potential difference between the anode and the cathode can exist without field emission from the cathode taking place, thereby permitting the pulsing of trigger 13 to determine the precise instant at which X-rays will be produced by source 10.

In the embodiment shown in FIG. 1, plasma produced when trigger 13 is pulsed is injected into the interior of the cathode, and will close the gap between the trigger electrode and the anode in less than about 1 $\mu$sec. While this arrangement is often satisfactory for shadowgraphic X-ray techniques, the very high current rates and rapid impedance collapse produced by injection of the plasma toward the anode sometimes has undesirable results when a source is to be used in a CT scanner.

One of the problems that has been noted experimentally are spikes in the current flow between the anode and the cathode. Such spikes may have a deleterious effect on the spectral, temporal, and spatial characteristics of the resultant X-rays. Improved results can be obtained by modifying the free end of the trigger electrode, and the orientation of the non-conducting surface interconnecting the electrode with the cathode.

Figure 2A:
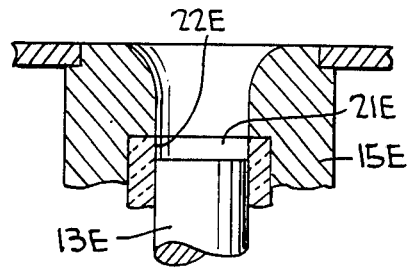
FIGS. 2A-B are cross-sectional views of different versions of surface flashover triggering.
Figure 2B:
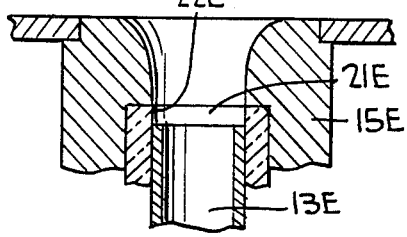

The orientation of the non-conducting surface affects the launch direction of the plasma. When the plasma is directed toward the anode, the probability of occurrence and the amplitude of current spikes increases. In FIG. 1, the normal to the non-conducting surface intersects the anode, which will tend to produce spikes. In FIG. 2A, the normal does not intersect the anode, reducing the tendency to produce spikes. A further improvement is shown in FIG. 2B, in which the trigger electrode rod is replaced by a hollow conducting cylinder. In this case, the plasma partially expands into the hollow cylinder rather than toward the anode.

All of the arrangements shown in FIGS. 1 and 2 utilize surface flashover (i.e., a voltage breakdown over a non-conducting surface) to trigger the generation of a burst of X-rays. The use of surface flashover is advantageous because it enables the origin of the plasma to be well-defined each time the X-ray source is triggered. As indicated above, it has been found experimentally that if the direction of plasma travel is directly toward the anode, current spikes are often produced in the anode-to-cathode current, thereby reducing the voltage and adversely affecting the spectral and spatial stability of the resultant X-rays, as well as reducing reproducibility of results. For image reconstruction, these deficiencies are often unsatisfactory, while the deficiencies have almost no effect when the X-ray source is used for obtaining shadowgraphs. If the plasma is not launched directly toward the anode, experiments have shown that there is a reduction in flux, and consequently a reduction in the X-ray output.

Figure 3:
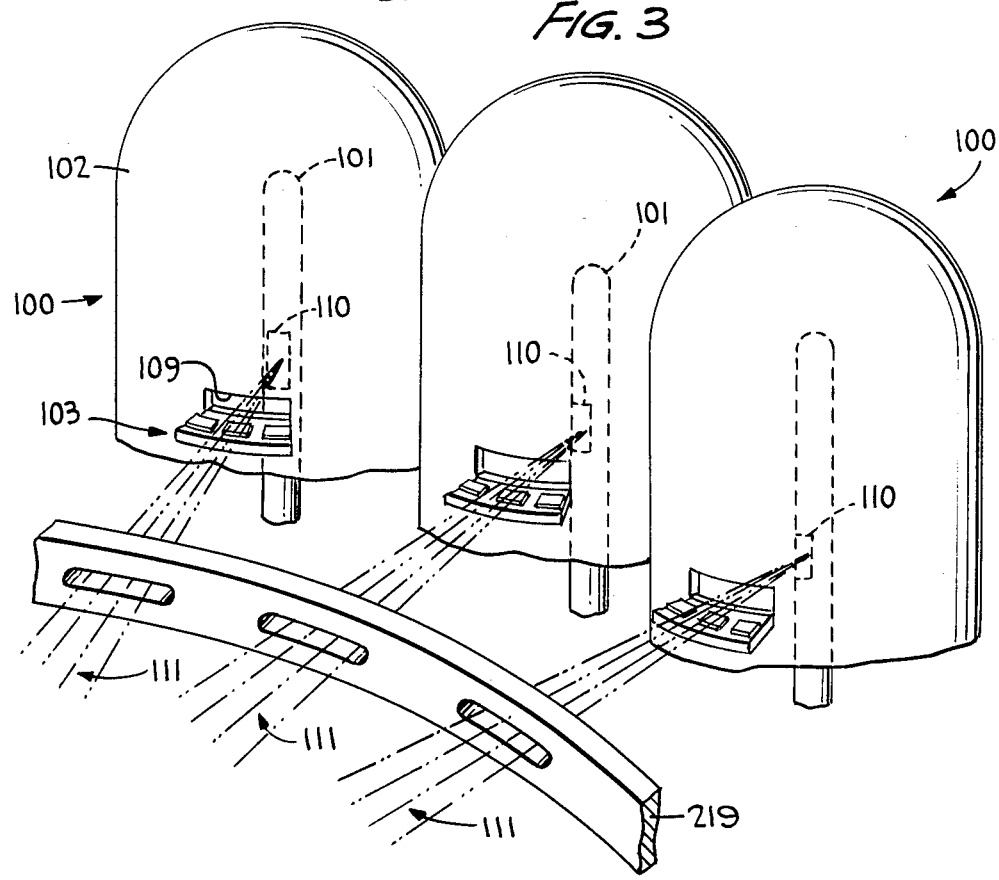
FIG. 3 is a perspective view of three sources according to the present invention illustrating another form of surface flashover triggering and the collimation of the resultant X-ray beams indicating the manner in which such sources are incorporated into a CT scanner.
Figure 7:
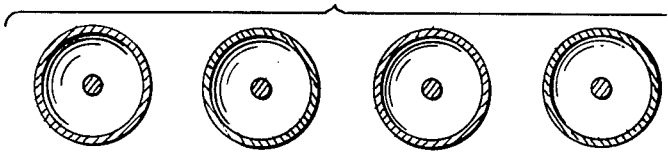
FIG. 7 is a sectional view taken along the line 7—7 of FIG. 8.

In order to eliminate current spikes often obtained with the devices shown in FIGS. 1 and 2, and to retard impedance collapse, which often occurs with some of these arrangements, the following configuration shown in FIG. 3 can be utilized. FIG. 3 shows a plurality of triggered plasma cathode flash X-ray sources 100, each source comprising an axially extending anode rod 101 supported in cantilever fashion from an anode bus (not shown), a cylindrical cathode sleeve 102 whose axis coincides with the axis of the anode rod, and trigger system 103. As shown in FIG. 4, system 103 is constituted by a plurality of conductive pads 104A-C separated by gaps 105A-B defined by nonconducting surface 106 of insulator 107, which may be in the form of a substrate similar to a printed circuit board. Substrate 107 is planar, and is provided with conductive plane 108 on the surface thereof opposite surface 106, as best shown in FIG. 5. Conductive plane 108 is maintained at the same potential as the cathode by a suitable electrical connection; and the substrate is fixed to the outer surface of cathode sleeve 102 by brackets or the like (not shown). Sleeve 102 is apertured as indicated by reference numeral 109 in the vicinity of gaps 105A and 105B between the conductive pads on the substrate.

When the voltage between anode 101 and cathode 102 is maintained at a relatively high value, such as 150 KV, and a trigger pulse of from 2-10 KV is applied to at least one of pads 104A-C, and at least one of the other of the pads (e.g., pad 104C) is held at the same potential as the cathode by a suitable connection to ground, sequential flashover will occur across gaps 105A and 105B, producing separate bursts of plasma exterior to the cathode sleeve, each burst being launched in a direction substantially perpendicular to the surface 106 of the substrate. Electrons present in the plasma are drawn through aperture 109 in the cathode sleeve toward anode 101 and impact the anode, producing omni-directional X-rays from a focal spot indicated by reference numeral 110. Some of these X-rays are indicated by lines 111 in FIG. 3.

Gaps 105A and 105B are relatively small (e.g., less than 1 mm). Generally speaking, the parallel capacitance between a pad and conductive plane 108 will significantly exceed the interstage capacitance between adjacent pads, with the result that the potential of pad 104B is essentially at ground. When a trigger pulse is applied to pad 104A, gap 105A fails, producing a plasma burst that makes electrons available for movement through aperture 109. When gap 105A breaks down, pad 104B is driven to the trigger voltage level, and the process repeats itself sequentially over the remaining gaps. Each time gap failure occurs, additional plasma is created, which enables additional electrons to flow between the cathode and the anode. The progression of gap failure between successive pads is almost instantaneous.

While FIG. 4 shows an arrangement with three conductive pads that are rectangular, the shape of the pads as well as their number (and consequently the number of gaps therebetween), can be selected to provide discrete plasma sources that are angularly distributed with respect to the anode. Because the diode current and X-ray flux increase as the number of discrete plasma sources increases, compensation is achieved for the reduction in current flow between the cathode and the anode which results when the surface flashover occurs outside the cathode sleeve. Moreover, experimental results show that current spikes produced with the previously described trigger electrodes are substantially eliminated. Furthermore, the resultant X-rays produced by sources like those shown in FIG. 5 exhibit improved spectral and spatial characteristics.

By changing the angular relationship between the plane of surface 106 of the substrate carrying the trigger and the axis of the anode, the angular direction in which the plasma is launched can be adjusted. Thus, if the angular relationship is an inclined one, a portion of the plasma produced by the flashover occurring at the gaps will pass through the aperture in the cathode and into the region between the anode and the cathode.

A CT tomographic scanner utilizing the coldcathode flash X-ray sources of the type shown in FIG. 3 is illustrated in FIG. 6. Scanner 200 in FIG. 6 comprises a hollow, evacuated annular shell 201 that houses a plurality of sources 100 arrayed about axis 202 of the scanner. The relationship between the axes of the anode rods and the axis 202 of the scanner can vary widely. For example, the axes of the anode rods can be parallel to the axis of the scanner, or the anodes can be arranged so that their axes are slightly inclined with respect to the axis of the scanner and intersect the axis at the same point. This is the arrangement shown in FIG. 6, and is selected to facilitate detection of the X-rays introduced as described below.

In order to mount the anodes in chamber 201, metallic anode ring 203 inside the chamber is utilized. Ring 203 is mechanically coupled to, but insulated from, housing 201, which is evacuated and maintained in this condition by vacuum pump 204. Each of anode rods 101 of sources 100 is mounted in cantilevered fashion to ring 203, to which high-voltage lead 205 is connected. Lead 205 passes through high-voltage bushing 206 in an end wall of chamber 201. When the scanner is to be operated in Mode II, described above, ring 203 is connected by lead 205, via crowbar device 227, to high-voltage source 207, which has the ability of generating a train of high-voltage (e.g., 150 KV) pulses. Crowbar device 227 is a controlled, normally open switch connecting the output of generator 207 to ground. Device 227, which may be a multi-gap thyratron tube, for example, is triggered by an output trigger pulse derived from driver 222 timed to occur during the trailing portion of the high voltage pulse. In response, the tail of the high-voltage pulse produced by generator 207 is shunted to ground.

Each of the anode rods is provided with an individual cathode sleeve 102A, which, as indicated above, is a cylinder of low-Z material such as aluminum. One end of the cathode is provided with a hemispherical dome 208, while the other end of the cathode adjacent ring 203 is provided with an outwardly flared skirt 209. Cathodes 102A are mechanically attached to chamber 201. A common structure interconnects all of the cathodes, which are held at ground potential.

Each of the cathodes is provided with at least one and preferably a plurality of slits facing axis 202. In order to simplify the drawing, only two slits 212 and 213 in each of the cathodes are shown. Adjacent respective slits are surface flashover triggers 214, 215 similar to the surface flashover trigger 103 shown in FIG. 3. That is to say, triggers 214 and 215 provide for distributed sources of plasma adjacent respective apertures 212 and 213. At least one of the conductive pads (not shown in FIG. 6) of each trigger is connected by a lead that passes through trigger bushing 216 in chamber 201. Thus, a trigger lead is provided for each trigger, the various leads passing through bushing 216 and being connected to trigger drive circuit 217 for the purpose of distributing trigger pulses to the various sources in synchronism with the high-voltage pulses furnished by source 207. While many trigger bushings 216 will be required, the voltages involved are relatively low as compared to the high-voltage bushing 206, of which only one is required.

Located on the inner circumferential surface 218 of chamber 201 is ring-shaped lead collimator 219, which is also shown in FIG. 3. Collimator 219 contains a set of slits 220 for each of the triggers utilized with X-ray sources lOOA. That is to say, for an arrangement in which each source is provided with two triggers, two sets of slits 220 are provided, as indicated in FIG. 6. Each set of slits limits the X-rays produced by a source to a fan beam having an angular spread measured in a plane perpendicular to axis 202 defined by the ring of X-ray detectors 221. Each fan beam also spreads in the direction of axis 202 so that each beam illuminates both sets of detectors as described below. The plane of the fan beam is essentially perpendicular to axis 202; and in FIG. 6, this angular relationship has been exaggerated for the purpose of clarity, it being understood that the plane of the fan beams produced by sources lOOA will be substantially perpendicular to the axis 202 of the scanner.

Ring-shaped detector array 221 is located on one axial end face of chamber 201, and is supported therefrom. Two sets of detectors are shown in ring 221. Because X-rays from each ring of apertures 212 and 213 irradiate both rings of detectors in ring 221, a total of four cross-sectional slices of patient 223 are imaged. A greater number of sections can be obtained by increasing, either the number of source rings, comprised of plasma triggers and X-ray apertures, or the number of detector rings. A plurality of sections through the patient thus may be obtained simultaneously or in rapid succession.

In operation, driver 222 causes source 207 to produce a train of high-voltage pulses which are applied to anode ring 203, and thus the anode rods of sources lOOA in parallel. Driver 222 also causes trigger voltage source 217 to sequentially apply trigger pulses to the various triggers of the X-ray sources in synchronism with the high-voltage pulses so that a rotating array of fan beams is obtained. As indicated in FIG. 6, the focal spots of the sources on the anodes due to triggers 214 lie in a common plane perpendicular to axis 202, while the focal spots due to triggers 215 lie in a plane perpendicular to axis 202 displaced from the first-mentioned plane. However, the fan beams due to trigger 214 trace out a somewhat conically shaped section through patient 223. The conical nature of this section is exaggerated in FIG. 6.

The output of detectors 221 is applied to analog-to-digital converters, as indicated by reference numeral 224, in a conventional manner. The digital signals are then applied to digital computer 225 for the purpose of accumulating all of the data produced by the scanner and operating on it according to a predetermined algorithm for the purpose of storing in memory 226 a representation of a reconstruction image of the scanned cross-section.

Figure 8:
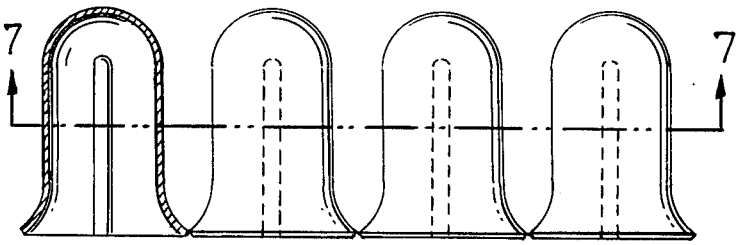
FIG. 8 is a side view of the development of one form of packing the sources around the axis of the scanner.
Figure 9:
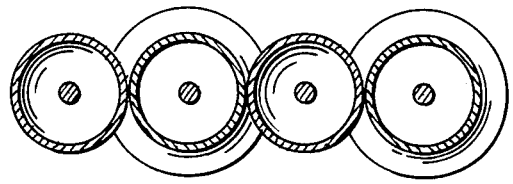
FIG. 9 is a sectional view taken along the line 9—9 of FIG. 10.
Figure 10:
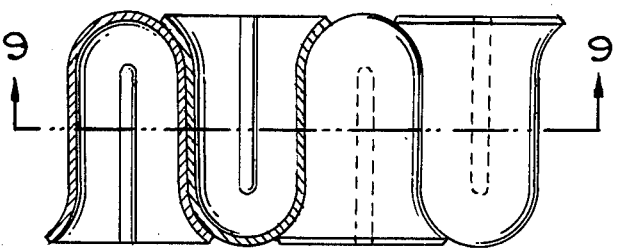
FIG. 10 is a side view of the development of a second way of packing the sources around the axis of the scanner.

In FIG. 6, the sources are packed around the axis of the scanner such that the closed ends of the cathodes face in one direction. This type of packing is illustrated in FIG. 8, which is a side view of a development of the anode bus. Note that the presence of the flared skirts forces the separation of the anodes to a dimension exceeding the diameter of a cathode. A more dense pattern can be achieved as shown in FIG. 10, wherein the closed ends of the cathodes of adjacent sources face in opposite directions. In this packing configuration, the spacing between anodes in adjacent sources is the same as the diameter of a cathode. This configuration requires two anode buses.

Figure 11:
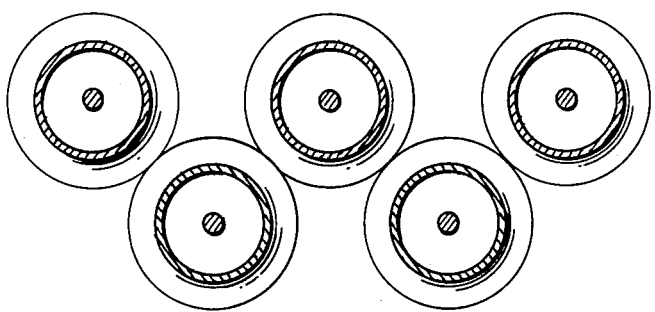
FIG. 11 is a third approach to packing the sources around the axis of the scanner.
Figure 12:
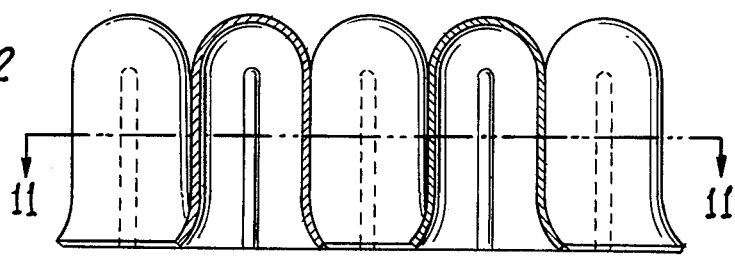
FIG. 12 is a plan view of the development of FIG. 11.

In order to achieve an even more dense packing, the rows of anode rods can be used as shown in FIG. 11. In this case, the anodes in one row are staggered or interleaved with respect to the anodes in the other row, as shown in FIG. 12.

Another embodiment of the invention is shown in FIG. 13 wherein a triggered plasma cathode flash X-ray source is designated by reference numeral 300. In this embodiment, source 300 includes a planar conductive plate 301 that constitutes the cathode of the source, rod 302 that constitutes the anode of the source, and trigger system 303. Plate 301 is apertured at 304, the aperture having a smoothly waved surface 305 that faces rounded nose 306 of anode 302 whose axis is aligned with the axis of aperture 304. The spacing between nose 306 and front surface 307 of the cathode is about 2 cm.; and the curved surfaces which face each other on the anode and cathode serve to reduce the concentration of the electric field lines thereby suppressing spurious firing of the source.

Secured to the rear surface of plate 301 overlying aperture 304 is insulating retainer 308 containing a centrally located hole within which trigger electrode 309 is mounted, the forward free end of the electrode projecting into aperture 304 but terminating below the plane of surface 307. Surrounding the trigger electrode adjacent the free end thereof is insulating disk 310 located within a depression defined by aperture 304. As seen in FIG. 13, the free end of electrode 309 extends just beyond the forward surface of disk 310 which provides a non-conducting surface across which flash over can take place when a predetermined trigger voltage is applied between plate 301 and trigger electrodes 309. Thus, nose 306 of the anode faces a depression in surface 307 of the cathode; and the normal to such surface in the region of the depression passes through the axis of rod 302.

In operation, a high voltage pulse, for example about 150 KV produced by a pulse forming network, is applied between anode 302 and cathode 301 which may be at ground potential. During the existence of the high voltage between the anode and cathode, a relativelty small trigger pulse, say 2-15 KV is applied between electrode 309 and cathode 301; and surface flashover occurs across the forward surface of disk 310 between the trigger electrode and the cathode plate. The resultant plasma burst 311 expands axially from the trigger electrode toward anode 302 providing a source of electrons that are accelerated toward and impact on a portion of hemispherical surface 306 of the anode producing a burst of X-rays that radiate omnidirectionally from the "focal spot" defined by the area of the surface 306 impacted by the electrons. Being formed of low-Z metal, plate 301 is transparent to the X-rays so formed; and by suitable shieldings, the preferred direction of the resultant X-rays is in the direction indicated by arrow 312.

The embodiment shown in FIG. 13 provides for directly launching plasma toward the anode. However, the basic configuration is adaptable to control the direction of launch of the plasma; and this is shown in FIG. 14. Source 300' includes plate cathode 301' containing aperture 304', anode 302', similar to the corresponding components in source 300 and trigger system 303 comprising insulator 319 interposed between return plane 320, and conductive pads 321 positioned eccentrically to aperture 304' with the pads just below the edge of aperture 304' on the rear face of plate 301'. Pads 321, which constitute a part of the trigger system, are of the type shown in FIG. 4 in that one or more gaps (not shown) exist between the pads and define the regions over which surface flashover occurs when a trigger pulse is applied between a conductive pad and the cathode plate. With this arrangement, plasma burst 311' is launched in a direction normal to the axis of anode 302'; but electrons in the plasma are drawn through aperture 304' toward the hemispherical end of anode 302' producing X-rays on impact.

The provision of a recess or depression in a locally flat cathode plate to localize the plasma bursts, as shown in FIGS. 13 and 14, allows a dense packing of sources when incorporating these embodiments of sources into a CT scanner. This is illustrated in FIG. 15 which shows a plurality of sources incorporated into a unitary device 330. Thus, device 330 includes a flat metallic strip 331 constituting a common cathode, and common anode 332. Cathode strip 331 contains a plurality of spaced apertures 304" that are similar in shape to apertures 304 and 304' previously described. Aligned with the axis of each aperture 304" is anode rod 333, each of the rods 333 being connected to bus 334. To assist in shaping the electric field lines in the region between front surface 307" of strips 331, the surface may be embossed with raised regions 335. The shape and location of these regions are selected so as to establish electric field lines that tend to focus electrons emerging from one of apertures 304" on the opposite anode.

FIG. 15 shows strip 331 in its developed position, it being understood that the strip could be curved with the center of curvature lying on the axis of the CT scanner. In such case, the anode rods would be radially positioned further from the axis of the CT scanner than strip 331.

FIG. 16 shows a modification of the embodiment of FIG. 15 wherein a multiple anode array is staggered to increase the packing density. The axis of reconstruction is designated by reference numeral 340; and cathode strip 331' circularly surrounds the axis and is concentric therewith. The cathode strip has two rows of apertures 304''', each aperture having an anode rod 333' associated therewith. The pitch of the apertures in each row is the same, but the apertures in one row are staggered with respect to the apertures in the other row thereby halving the effective pitch.

In operation, a trigger system (not shown) on the surface of strip 331' is associated with each aperture for selectively creating plasma bursts within or closely adjacent to the apertures. Each plasma burst provides electrons that are accelerated toward and impact on an opposite anode producing X-rays that radiate omnidirectionally from the free ends of the opposite anode. By suitable shielding, a fan beam of radiation would be produced for each anode, the various fan beams being essentially coplanar. FIG. 16 distorts this relationship because axis 340 is shown so close to the sources in relation to the pitch between the apertures in the cathode strip and the axis spacing between the rows.

Another embodiment of the invention is shown in FIG. 17 for obtaining multiple slices through a patient without indexing the patient. Here, annular evacuated envelope 350 contains a plurality of sources each having a cathode and anode and a trigger system. Specifically, the cathode is in the form of a metallic band 351 facing a plurality of rods 353 mounted on a metallic band 354 of a diameter greater than the diameter of band 351. Associated with each aperture 352 in band 351 is a trigger system 355 for selectively producing a burst of plasma that results in X-rays in response to a trigger signal applied from generator 356. Slit structure 357 limits the output of each source to a fan beam 358, these fan beams lying in planes that are essentially normal to the axis of the scanner.

Trigger system 355 can take the form shown in FIG. 13 or FIG. 14. In either case, band 351 has surface 359 containing depressions respectively associated with anode rods 353. The normals to surface 359 in the vicinity of the depressions pass through the respective axes of the rods as shown in FIG. 17.

Although only two source rings are shown and described, additional source rings may be implemented to increase the number of sections through the body.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

What is claimed is:

1. A medical imaging device comprising:
 (a) a plurality of triggered plasma cathode X-ray sources each having an anode and a cathode;
 (b) an electrical network including a high voltage source for applying a predetermined voltage between all of the anodes as a group and all of the cathodes as a group;
 (c) the electrical network also including a separate trigger system associated with each source and constructed and arranged so that, in response to the application of a trigger pulse to the trigger system of a selected source, a burst of plasma is created adjacent the cathode of the selected source, the predetermined voltage between the anode and cathode of the selected source causing electrons in the plasma to be accelerated toward and impact on the anode of the selected source at a focal spot thereby producing a burst of X-rays; and
 (d) a plurality of detectors for receiving X-rays produced by the sources and producing output signals inresponse thereto.

2. A medical imaging device according to claim 1 wherein the sources and the detectors are arrayed about the axis of the device, and the X-rays produced pass through the axis of the device.

3. A medical imaging device according to claim 1 in which means is used to reduce anode damage by diverting low energy electrons away from the anode.

4. A medical imaging device according to claim 1 wherein the cathodes are constituted by a metallic strip having a surface facing the anodes containing a plurality of depressions associated with and opposite respective anodes, the normals to the surface in the vicinity of the depressions passing through the axes of respective anodes.

5. A medical imaging device according to claim 4 wherein the strip is curved into a circular shape whose center defines the axis of the scanner.

6. A medical imaging device according to claim 5 wherein the anodes are arranged in axially displaced rows.

7. A medical imaging device accoreing to claim 5 wherein the anodes in one row are radially displaced and circumferentially staggered with respect to the anodes in another row.

8. A medical imaging device comprising:
   (a) a plurality of triggered plasma cathode X-ray sources each having an anode and a cathode;
   (b) an electrical network including a high voltage source for applying a predetermined voltage between all of the anodes as a group and all of the cathodes as a group;
   (c) the electrical network also including a separate trigger system associated with each source and constructed and arranged so that, in response to the application of a trigger pulse to the trigger system of a selected source, a burst of plasma is created adjacent the cathode of the selected source, the predetermined voltage between the anode and cathode of the selected source causing electrons in the plasma to be accelerated toward and impact on the anode of the selected source at a focal spot thereby producing a burst of X-rays;
   (d) a plurality of detectors for receiving X-rays produced by the sources and producing output signals in response thereto.
   (e) the sources and the detectors being arrayed about the axis of the device; and
   (f) the tirgger system associated with each source being constructed and arranged so that surface flashover occurs in response to the application of a trigger pulse to the trigger system of a selected source for creating burst of plasma adjacent the cathode of the selected source.

9. A medical imaging device according to claim 8 wherein each trigger system has a trigger electrode to which a trigger pulse can be applied, and a non-conductive surface that interconnects the trigger electrode with a conductor held at the same potential as the cathode with which the trigger system is associated.

10. A medical imaging device of claim 9 wherein the sources are arranged in a plurality of axially displaced groups such that the focal spots on the anodes of each group define axially displaced planes.

11. A medical imaging device according to claim 9 including means for optically shielding the anodes of adjacent sources.

12. A medical imaging device according to claim 11 wherein the means for optically shielding the anodes are cathode sleeves at least partially surrounding the respective anodes.

13. A medical imaging device according to claim 12 wherein the anodes are round or essentially round rods.

14. A medical imaging device of claim 13 wherein the sources are arranged in two groups such that the focal spots on the anodes of one group define one plane substantially perpendicular to the axis of the scanner, and the focal spots on the anodes of the other group define another plane substantially perpendicular to the axis of the scanner, the one and the other planes being axially displaced.

15. A medical imaging device according to claim 15 including a collimator associated with each source for collimating X-rays emanating from the focal spot on the anode of the source into a fan beam.

16. A medical imaging device of claim 13 wherein the sources are arranged in more than two groups such that the focal spots on the anodes of one group define one plane substantially perpendicular to the axis of the scanner, and the focal spots on the anodes of the other groups define other planes substantially perpendicular to the axis of the scanner, the one and the other planes being axially displaced.

17. A medical imaging device of claim 16 wherein the detectors are arranged in a ring whose axis coincides with the axis of the scanner, and which is displaced from the sources axially of the scanner.

18. A medical imaging device according to claim 13 wherein the sources are arrayed in a single group such that the focal spots on the anodes of each source in the group define a plane perpendicular to the axis of the scanner.

19. A medical imaging device of claim 18 wherein the axes of the anodes are substantially parallel to the axis of the scanner.

20. A medical imaging device according to claim 12 wherein the axes of the anodes intersect the axis of the scanner at the same point.

21. A medical imaging device according to claim 13 wherein the cathode of each source is a cylindrical sleeve, the axis of which coincides with the axis of the anode of the source, each sleeve of the source being apertured in the vicinity of the trigger electrode of the source, the electrode and non-conducting surface of each source being outside the sleeve of the source and radially closer to the axis of the scanner than the anode.

22. A medical imaging device of claim 21 wherein each of the cathodes is closed at one end by a hemispherical dome, and is provided with an outwardly flaring skirt at the other end.

23. A medical imaging device of claim 22 wherein the sources are arranged such that the hemispherical domes face in the same axial direction of the scanner.

24. A medical imaging device of claim 22 wherein the sources are arranged such that the domes of adjacent sources face in opposite axial directions of the scanner.

* * * * *